(12) United States Patent

Paulus et al.

(10) Patent No.: US 9,535,017 B2
(45) Date of Patent: Jan. 3, 2017

(54) METHOD AND APPARATUS FOR CHARACTERISING A MATERIAL BY SCATTERING OF ELECTROMAGNETIC RADIATION

(71) Applicant: Commissariat A L'Energie Atomique Et Aux Energies Alternatives, Paris (FR)

(72) Inventors: Caroline Paulus, Grenoble (FR); Joachim Tabary, Grenoble (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 97 days.

(21) Appl. No.: 14/352,774

(22) PCT Filed: Oct. 19, 2012

(86) PCT No.: PCT/IB2012/055752
§ 371 (c)(1),
(2) Date: Apr. 18, 2014

(87) PCT Pub. No.: WO2013/057716
PCT Pub. Date: Apr. 25, 2013

(65) Prior Publication Data
US 2014/0369473 A1 Dec. 18, 2014

(30) Foreign Application Priority Data

Oct. 21, 2011 (FR) ..................................... 11 03248

(51) Int. Cl.
*G01N 23/203* (2006.01)
*G01N 23/20* (2006.01)
(52) U.S. Cl.
CPC ...... *G01N 23/20091* (2013.01); *G01N 23/203* (2013.01); *G01N 23/20066* (2013.01); *G01N 2223/063* (2013.01); *G01N 2223/601* (2013.01)

(58) Field of Classification Search
CPC .... G01N 23/20; G01N 23/203; G01N 23/207; G01N 23/201; G01N 23/04; G01N 23/08; G01N 23/20066; G01N 23/20091; G01V 5/0025

(Continued)

(56) References Cited

U.S. PATENT DOCUMENTS

2012/0123697 A1\* 5/2012 Fabiani ............... G01N 23/203
702/28

FOREIGN PATENT DOCUMENTS

WO WO 2011/009833 A1 1/2011

OTHER PUBLICATIONS

International Search Report from International Application No. PCT/IB2012/055752, mailed Feb. 5, 2013.

(Continued)

*Primary Examiner* — Jurie Yun
(74) *Attorney, Agent, or Firm* — Alston & Bird LLP (57) ABSTRACT

The invention relates to a device for identifying a material of an object having: a source of X photons and a spectrometric detector, the source irradiating the object with an incident beam and the detector measuring a magnitude of a backscattered beam from the incident beam after diffusion in a volume of the material and an energy of the X photons of the backscattered beam, the incident and backscattered beams forming an angle of diffusion (θ); a configuration for adjusting the position between the source, the detector and the object in order for the volume to be at different depths with a constant angle, a means for processing the two magnitudes in two positions and the energy in on position and for calculating an attenuation factor (μmateriau (E0, E1, (Continued)

ϵ)), a configuration for estimating the density (p) of the material.

15 Claims, 6 Drawing Sheets

(58) Field of Classification Search
    USPC .......................... 378/70, 82, 86, 87, 88, 89
    See application file for complete search history.

(56) References Cited

OTHER PUBLICATIONS

Written Opinion from International Application No. PCT/IB2012/055752 mailed Feb. 5, 2013.
Li, Wei et al: "Partial Least-Squares Regression for Identification of Liquid Materials"; Procedia Engineering; vol. 7; Jan. 1, 2010; pp. 130-134; XP055025646.
Rebuffel, Veronique et al: "New Perspectives of X-Ray Techniques for Explosive Detection Based on CdTe/CdZnTe Spectrometric Detectors"; International Symposium on Digital Industrial Radiology and Computed Tomography; vol. 8; Jun. 22, 2011; p. 1; XP055025669.
Luggar, R.D. et al.; "Multivariate Analysis of Statistically Poor EDXRD Spectra for the Detection of Concealed Explosives"; X-Ray Spectrometry; vol. 27, No. 2; Mar. 1, 1998; pp. 87-94; XP055025645.

\* cited by examiner

METHOD AND APPARATUS FOR CHARACTERISING A MATERIAL BY SCATTERING OF ELECTROMAGNETIC RADIATION

FIELD

The invention relates to a method for characterizing a material, and notably an organic material, by scattering of electromagnetic radiation, and notably of X-rays. The invention also relates to a device for the implementation of such a method.

The characterization can comprise the identification of the material within a database, or simply the determination of one or more of its physical or physico-chemical properties, such as its density.

The invention is mainly applicable to the characterization of "light" materials, and notably organic materials. The term "light materials" is understood to mean materials constituted at 90% by mass or more by atoms of atomic number less than or equal to 10, and "organic materials" the materials constituted at 90% by mass or more of carbon or carbon compounds. The invention is in particular applicable to the materials referred to as "CHON materials", composed exclusively, or almost exclusively (at 95% by mass or more), of carbon (C), hydrogen (H), oxygen (O), nitrogen (N), or to fluorinated light organic materials comprising these same elements plus fluorine.

The invention can use any type of electromagnetic radiation having a sufficiently high (photon) energy, in other words greater than or equal to 1 keV (kiloelectronvolt; 1 keV=$1.602 \times 10^{-16}$ J), preferably greater than or equal to 10 keV and more preferably in the range between 10 keV and 300 keV. Typically, the radiation can be X-rays, notably generated by an X-ray tube.

BACKGROUND

The document WO 2011/009833 describes a method of identification of a material by scattering of X-rays. According to this method, a collimated polychromatic beam (or polyenergetic, the two terms being synonymous) of X-rays is directed towards a sample of a material to be identified. A part of the incident X-rays are subjected to Compton scattering inside of the material, and the photons scattered through a predefined scattering angle θ are detected by a spectrometric sensor. The collimated incident beam and the acceptance cone of the sensor, which is narrow (a few degrees), define an elementary volume inside of the sample, from where all the photons detected originate. The source of the beam of X-rays and the spectrometric sensor are displaced perpendicularly to a surface of the sample while keeping their orientation constant; in this way, the depth of said elementary volume is varied with respect to said surface of the sample; a spectrum of scattered X-rays is acquired for each said depth. The knowledge of two spectra corresponding to different depths allows two parameters μ' and β, functions of the energy of the scattered photons, to be directly calculated.

It has been shown that, for a given energy and for a large number of known materials, μ' is approximately proportional to the density of the material. This allows the density ρ—unknown—of the material to be characterized, to be estimated, starting from the value of μ' averaged over a predefined range of energy. Furthermore, the knowledge of said density ρ and of the parameter β allows the ratio $Z_{eff}/A_{norm}$ to be determined, where $Z_{eff}$ is the effective atomic number of a material (a quantity which characterizes its interaction with X-rays) and $A_{norm}$ its normalized molar mass. Thus, the material may be represented by a point in a plane $\rho/(Z_{eff}/A_{norm})$, whose coordinates are determined based on at least two spectra of scattered X-rays. This allows the identification of the material.

SUMMARY

The invention aims to supply an alternative to this method, by allowing a more precise characterization of the material thanks to a better exploitation of the information contained in the scattering spectra.

According to the invention, such an aim is achieved by a method for characterizing a material comprising the steps consisting in:

a. directing a first collimated beam of electromagnetic radiation, of energy greater than or equal to 1 keV, towards a sample of the material to be characterized;

b. acquiring the spectrum of a second beam of electromagnetic radiation, obtained by scattering of said first beam by an elementary volume of said sample through a predefined scattering angle θ;

said steps a and b being repeated one or more times, each time modifying the lengths of the paths of the first and of the second beam inside of said material, while at the same time maintaining substantially constant their ratio ε together with said scattering angle θ; and c. estimating one or more properties characteristic of said material based on the spectra acquired during the repetitions in the step b;

characterized in that said step c is implemented by means of at least one multivariate model.

According to various embodiments of this method:

Said step c can comprise the calculation, using the spectra acquired during the repetitions of said step b, of a combined linear extinction function μ' of the material, defined as a weighted average of the linear extinction coefficients μ of the material for the electromagnetic radiation incident at an energy $E_0$ and for the electromagnetic radiation scattered at an energy $E_1$, where $E_0$ represents the energy of an incident photon and $E_1$ that of a photon having undergone a scattering through said scattering angle θ, the weighting coefficients of said average depending on said ratio ε, said combined linear extinction being expressed as a function of an energy chosen from between $E_0$ and $E_1$. The step c can also comprise the estimation of the density of said material based on the values of said combined linear extinction function for a plurality of values of energy, by application of a first multivariate model. In the method known from the prior art, on the other hand, the density ρ of the material is simply considered to be proportional to the average value of μ'; the averaging operation leads to a loss of information which, in the method of the invention, is avoided thanks to the use of a multivariate model.

Said step c can also comprise: the determination of a function Dμ' representative of a comparison between values taken by said combined linear extinction function μ' for values of energy having a constant difference dE; and the estimation of a mass effective atomic number of said material based on the values of said function Dμ' for a plurality of values of energy, by application of a second multivariate model. Here again, the use of a multivariate model allows the loss of information inherent in the method of the prior art to be avoided.

The method can also comprise a step d for identification of said material based on the estimated values of its density and of its mass effective atomic number.

Said or at least a said multivariate model can be based on a regression by partial least squares, or PLS.

Said steps a and b can be repeated one or more times, each time modifying the depth of said elementary volume of the sample with respect to a surface of incidence of said collimated beam of electromagnetic radiation. In particular, said depth of said elementary volume of the sample can be modified by rigid translation of a source and of a spectrometric sensor of electromagnetic radiation with respect to said sample, in a direction perpendicular to said surface of incidence.

Said material can be an organic material.

Said first collimated beam of electromagnetic radiation can be polychromatic and can exhibit an energy spectrum extending over at least 10 keV in a region within the range between 10 keV and 300 keV.

Another subject of the invention is a device for characterizing a material comprising: a collimated source of electromagnetic radiation, configured for directing a first collimated beam of electromagnetic radiation towards a sample of the material to be characterized; a spectrometric sensor for electromagnetic radiation, configured for acquiring the spectrum of a second beam of electromagnetic radiation, obtained by scattering of said first beam by an elementary volume of said sample through a predefined scattering angle; an actuation system, configured for modifying the relative position of said source and of said spectrometric sensor with respect to said sample in such a manner as to modify the lengths of the paths of the first and of the second beam inside of said material, while at the same time maintaining substantially constant their ratio $\epsilon$ together with said scattering angle $\theta$; and a means for processing the information, configured or programmed for estimating one or more properties characteristic of said material based on a plurality of spectra acquired by said spectrometric sensor for various values of said lengths of the paths of the first and of the second beam inside of said material;

characterized in that said means for processing the information is configured or programmed for estimating one or more properties characteristic of said material by means of at least one multivariate model.

According to various embodiments of this device:

Said means for processing the information can be configured or programmed for calculating, based on the spectra acquired during the repetitions of said step b, a combined linear extinction function $\mu'$ of the material, defined as a weighted average of the linear extinction coefficients $\mu$ of the material for the electromagnetic radiation incident at an energy $E_0$ and for the electromagnetic radiation scattered at an energy $E_1$, where $E_0$ represents the energy of an incident photon and $E_1$ that of a photon having undergone scattering through said scattering angle $\theta$, the weighting coefficients of said average depending on said ratio $\epsilon$, said combined linear extinction being expressed as a function of an energy chosen from between $E_0$ and $E_1$.

Said means for processing the information can be configured or programmed for estimating the density of said material based on the values of said combined linear extinction function for a plurality of values of energy, by application of a first multivariate model.

Said means for processing the information can be configured or programmed for: determining a function $D\mu'$ representative of a comparison between values taken by said combined linear extinction function $\mu'$ for values of energy having a constant difference dE; and estimating a mass effective atomic number of said material based on the values of said function $D\mu'$ for a plurality of values of energy, by application of a second multivariate model.

Said means for processing the information can be configured or programmed for identifying said material based on the estimated values of its density and of its mass effective atomic number.

Said or at least a said multivariate model can be based on a regression by partial least squares, or PLS.

Said actuation system can be designed to modify the depth of said elementary volume of the sample with respect to a surface of incidence of said collimated beam of electromagnetic radiation by rigidly translating said source and said spectrometric sensor with respect to said sample, in a direction perpendicular to said surface of incidence.

Said collimated source of electromagnetic radiation can be polychromatic and exhibits an energy spectrum extending over at least 10 keV in a region within the range between 10 keV and 300 keV.

BRIEF DESCRIPTION OF THS DRAWINGS

Other features, details and advantages of the invention will become apparent upon reading the description that makes reference to the appended drawings presented by way of example, in which.

DETAILED DESCRIPTION

Throughout the description that follows, reference will be made to the case where the electromagnetic radiation is X-ray radiation.

Figure 1:
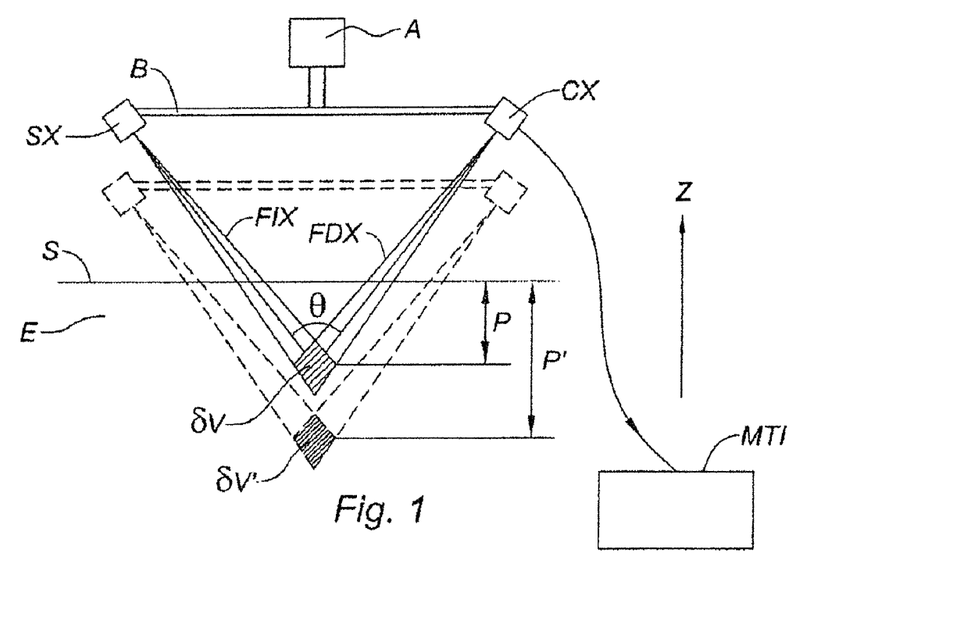
FIG. 1 shows schematically a device according to one embodiment of the invention.

The device illustrated in FIG. 1 mainly comprises a source SX of X-rays, a spectrometric sensor for X-rays CX, a structure B connecting the source and the sensor, an actuation means A for translating said structure in a direction Z and a means for processing the information MTI for receiving and processing signals coming from the sensor CX. This means for processing the information can be a appropriately programmed computer, an electronic board comprising a processor—general-purpose or application-specific for the digital processing of the signals—appropriately programmed, or even a digital electronic circuit appropriately configured.

The source SX is polychromatic (or polyenergetic) and collimated, and emits within the range 10 keV and 300 keV. It may be a conventional X-ray tube equipped with a collimation system; it emits a beam of X-rays FIX in the direction of a sample E of the material to be characterized. The divergence of the beam (angle at the apex of the cone formed by the X-rays) is typically less than or equal to 10°.

The sensor CX can be a semiconductor detector of the CdTe or CdZnTe type equipped with a collimation system which defines an acceptance cone FDX whose angular width (angle at the apex) is typically less than or equal to 10°. The axes of the beam FIX, incident on the sample, and of the acceptance cone FDX form an angle θ between them; their intersection defines an elementary volume δV which is located at a depth P below a surface S of the sample.

The X-ray photons generated by the source SX penetrate into the sample via the surface S, then undergo scattering phenomena—mainly of the Compton type—and absorption. It is straightforward to verify that, if the multiple scattering events are neglected, only the photons that are scattered inside of the elementary volume δV through a scattering angle approximately equal to θ can reach the spectrometric sensor θ and be detected.

The source SX and the sensor CX are mounted, with an adjustable orientation, on the structure B. An actuation means A, such as a linear electric motor, allows said structure to be translated in the direction Z, perpendicular to the surface S of the sample—or conversely, said sample to be translated in the same direction. The effect of this translation is to modify the depth P' of the elementary scattering volume, δV'. In the figure, the translated structure with its source and its sensor, together with the elementary volume δV', are shown with dashed lines.

Let $\Phi(E_0)$ be the flux density—unknown—of the source SX at the energy $E_0$. The flux of scattered photons that reaches the sensor CX is given by:

$$X(E_1) = \Phi(E_0) \cdot e^{-\mu(E_0) \cdot l_1} \left[ \frac{d\sigma_{Kn}(E_0, \theta)}{d\Omega} \delta\omega \frac{N_a \cdot Z_{eff\_a} \cdot \rho}{A_{norm}} \cdot \delta V \right] \cdot e^{-\mu(E_1) \cdot l_2} \quad (1)$$

where:

$$E_1 = \frac{E_0}{1 + \alpha(1 - \cos\theta)},$$

with $\alpha = \frac{E_0}{m_e c^2}$, $m_e$ being the mass of the electron and c the speed of the light, is the energy after Compton scattering;

$\mu(E_0)$ and $\mu(E_1)$ are the linear extinction coefficients of the material traversed before and after the scattering, respectively;

$l_1$ is the length of the path followed in the material by the photons before the scattering;

$l_2$ is the length of the path followed in the material by the photons after scattering;

$$\frac{d\sigma_{KN}}{d\Omega}(E_0, \theta)$$

is the differential scattering cross section per electron by Compton effect, given by the Klein-Nishina formula;

δω is the solid angle under which the detector is seen from the elementary scattering volume;

$N_a$ is Avogadro's number;

$A_{norm}$ is the normalized molar mass of the mixture defined by:

$$A_{norm} = \sum_i \alpha_i^{at} A_i,$$

where the factors $\alpha_i$ are the atomic proportions of the various elements, indexed by "i", which constitute the material;

$Z_{eff\_a}$ is the effective atomic number defined as $A_{norm}$ by:

$$Z_{eff\_a} = \sum_i \alpha_i^{at} Z_i;$$

and

ρ is the density of the material.

Figure 2:
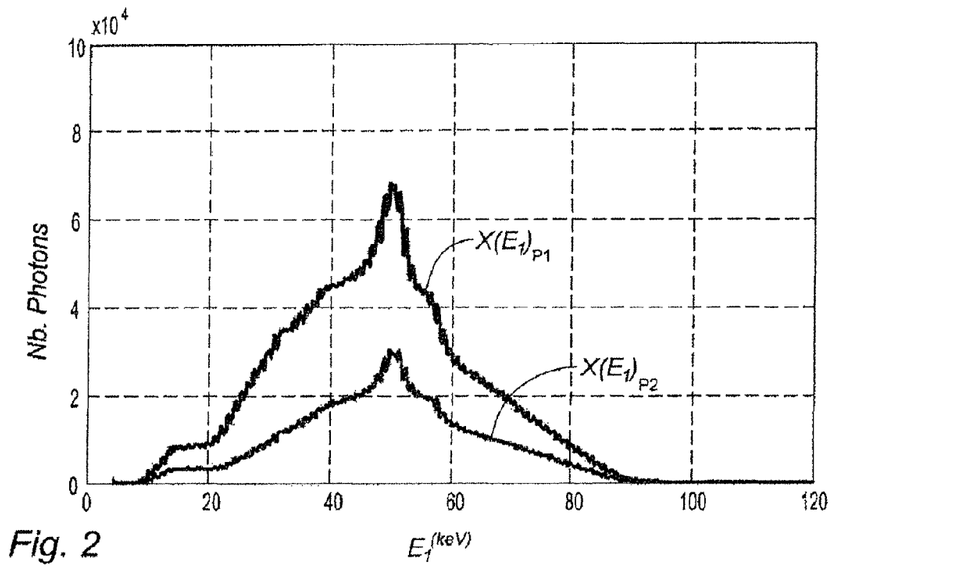
FIG. 2 shows two X-ray scattering spectra, corresponding to two different depths of the elementary volume of the material from where the detected scattered photons originate.

FIG. 2 shows the spectra of scattered X-rays corresponding to two different values of the depth of the elementary volume δV, $X(E_1)_{P1}$ and $X(E_1)_{P2}$.

By grouping all the independent terms of the material into a single coefficient denoted $K(E_1)$, the equation (1) is simplified and becomes:

$$X(E_1) = K(E_1) \cdot \frac{\rho \cdot Z_{eff\_a}}{A_{norm}} e^{-\mu'(E_1) \cdot l_2} \quad (2)$$

The "asymmetry factor" is defined as $\epsilon = l_2/l_1$ and the combined linear extinction function is defined as $\mu'(E_1) = \mu(E_1) + \epsilon \cdot \mu(E_0)$. As will be shown further on, this function contains all the information necessary for the characterization of the material. Furthermore, it can be estimated simply. For this purpose, two measurements of scattering spectra just need to be performed at two different depths, $X(E_1)_{P1}$ and $X(E_1)_{P2}$, making sure to keep constant both the angle θ and the asymmetry factor $\epsilon$; $\mu'(E_1)$ can then be calculated be means of the following equation:

$$\mu'(E_1) = \frac{\ln\left(\frac{X_{P1}(E_1)}{X_{P2}(E_1)}\right)}{l_2(P_1) - l_2(P_2)} = \frac{\ln\left(\frac{X_{P1}(E_1)}{X_{P2}(E_1)}\right)}{\Delta l} \quad (3)$$

where $l_2(P_1)$ is the length of the path followed within the material by the photons after scattering when the elementary scattering volume is located at the depth $P_1$, and $l_2(P_2)$ is the length of the path followed within the material by the photons after scattering when the elementary scattering volume is located at the depth $P_2$, and where "ln" indicates the Neperian or natural logarithm.

The displacement of the system between the two measurements is known, so that the step difference Δl is then also known.

The calculation of $\mu'(E_1)$ can be generalized with N>2 measurements at N depths. Indeed, the following can be written:

$$\ln(X(E_1)) = \ln\left(K(E_1) \cdot \frac{\rho \cdot Z_{eff\_a}}{A_{norm}}\right) - \mu'(E_1) \cdot l_2 \quad (4)$$

Thus, by measuring several spectra $X_i(E_1)$ at several depths $l_2(P_i)$, with $i=1 \ldots N$, the extinction curve $\mu'(E_1)$ can then be obtained by linear regression.

The asymmetry factor may also then be defined as $\epsilon' = l_2/l_1$, which then leads to: $\mu'(E_1, \epsilon') = \epsilon' \cdot \mu(E_1) + \mu(E_0)$. The step difference $\Delta l$ is then such that $\Delta l = l_1(P_2) - l_1(P_2)$, where $l_1(P_1)$ and $l_1(P_2)$ are the lengths of the path followed by the photons X within the material before scattering at the depth $P_1$ and $P_2$, respectively. Subsequently, it will be considered that $\epsilon = l_1/l_2$.

The identification of a material may be carried out by estimating two characteristic parameters, and by representing the material by a point in a plane whose two dimensions correspond to said parameters. The choice of the parameters is not completely arbitrary: the latter must be chosen in such a manner that two different materials are effectively represented by separate points. According to one preferred embodiment of the invention, the two parameters allowing the identification of the materials can be the density $\rho$ and the mass effective atomic number $Z_{effm}$. The density does not require any particular comments, it being simply the mass per unit volume of the material; the mass effective atomic number is defined by:

$$Z_{effm} = \sum_i \omega_i \cdot Z_i \quad (5)$$

where $Z_i$ is the atomic number of the i-th element constituting the material, and $\omega_i$ its proportion by mass in the material.

Figure 3:
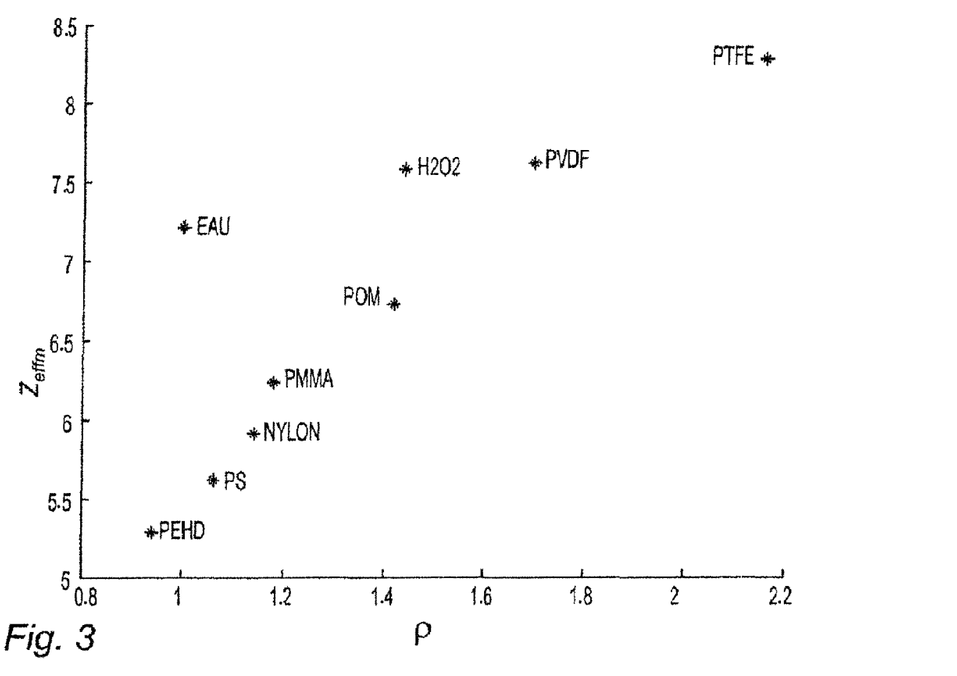
FIG. 3 show how various materials may be represented by points in a plane $\rho/Z_{effm}$, where $\rho$ is the density and $Z_{effm}$ the mass effective atomic number.

FIG. 3 shows several common organic materials in the form of points in the plane $\rho/Z_{effm}$: polyethylene (PHED), polystyrene (PS), nylon, polymethylmethacrylate (PMMA), polyvinylidenefluoride (PVDF), polyoxymethylene (POM), water, hydrogen peroxide (H2O2), polytetrafluoroethylene (PTFE).

The choice of these two parameters is advantageous for two reasons; on the one hand, as illustrated by FIG. 3, they allow various organic materials to be effectively differentiated; furthermore, they are linked to the combined linear extinction function $\mu'(E_1)$ by empirical relationships.

Figure 4A:
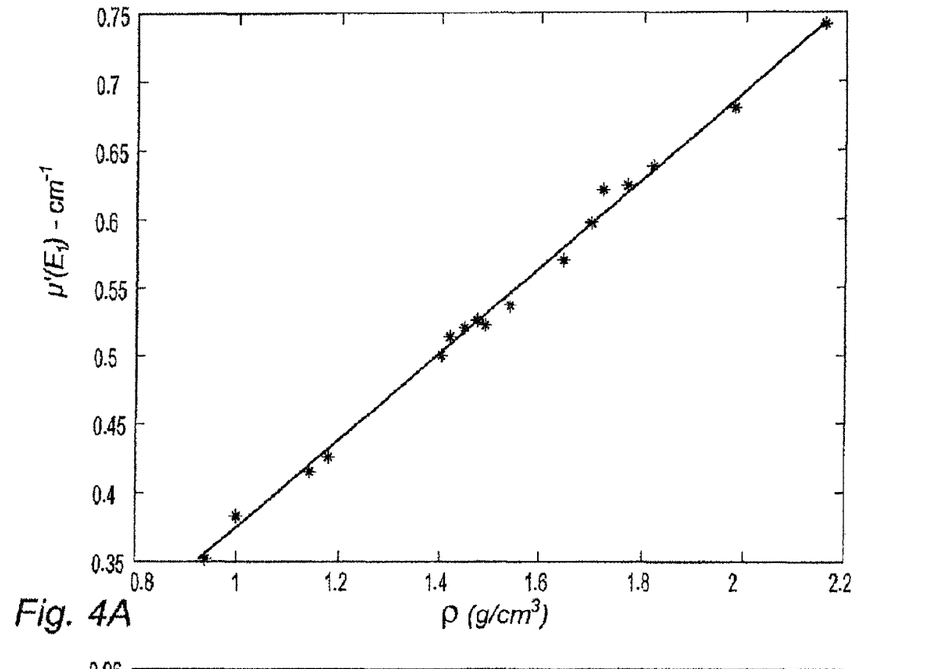
FIGS. 4A and 4B illustrate the empirical relationships existing between $\mu'$ and the density $\rho$, and between $D\mu$ and the mass effective atomic number $Z_{effm}$ for a set of materials.

FIG. 4A shows the correspondence existing between the combined linear extinction function, averaged between 50 and 80 keV, and the density for a set of materials. Each point represents one of the materials in FIG. 3, and the straight line has been obtained by linear regression; the standard deviation of the regression is equal to 0.0063626. Indeed, in the method of the aforementioned document WO 2011/009833, the density $\rho$ of the material to be identified is estimated based on an average value of the combined linear extinction function, calculated over a range of energy. However, as has been mentioned hereinabove, such an approach does not allow an optimal use of the information contained in the function $\mu'(E_1)$.

The empirical relation between the mass effective atomic number $Z_{effm}$ and the combined linear extinction function $\mu'(E_1)$ is less direct. In order to highlight it, a function $D\mu'$ first of all needs to be defined that is obtained from the combined linear extinction function and defined by:

$$D\mu'(E_1) = \frac{\mu'(E_1 + dE)}{\mu'(E_1)} \quad (6)$$

where $dE$ is a constant difference or increment in energy, which—by way of non-limiting example—can be equal to 5 keV and, more generally, in the range between 1 and 10 keV.

Figure 4B:
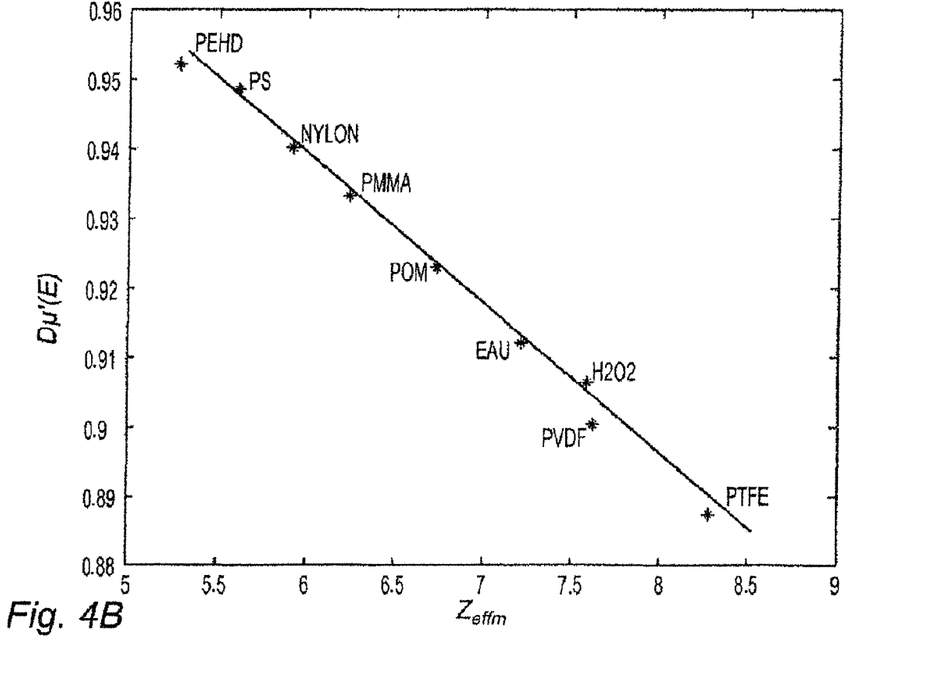

FIG. 4B shows the correspondence existing between the function $D\mu'$, averaged between 35 and 45 eV with $dE=5$ eV, and the mass effective atomic number $Z_{effm}$. What has been said hereinabove with regard to the loss of information caused by the energy averaging operation is also applicable to the estimation of $Z_{effm}$.

More generally, in order to obtain an estimation of $Z_{effm}$, a function $D\mu'$ is established that is representative of a comparison between values of $\mu'$ at different energies. This comparison is understood notably to mean the calculation of a difference or of a ratio between two quantities.

Another possible definition of $D\mu'$ is:

$$D\mu'(E_1) = \frac{\frac{d\mu'(E_1)}{dE_1}}{\mu'(E_1)}, \quad (6')$$

where $$\frac{d\mu'(E_1)}{dE_1}$$

is the derivative of the function $\mu'(E_1)$ with respect to the energy.

In order to best exploit the information available, contained in the measurements of scattering spectra, the method of the invention makes use of one or more multivariate models, or of factorial analysis, connecting the unknowns ($\rho$, $Z_{effm}$) to the variables which can be obtained directly from the measurements ($\mu'$, $D\mu'$).

Two steps are needed. The first, called calibration, corresponds to the construction of the mathematical model starting from the calibration curves corresponding to known materials (both the values $\rho$, $Z_{effm}$ and the functions $\mu'$, $D\mu'$ are then known). The second step, called prediction, enables the density $\rho$ and/or the mass effective atomic number $Z_{effm}$ to be estimated for unknown materials using the curves $\mu'/D\mu'$ obtained based on the measured scattering spectra and the model constructed at the calibration step.

The learning method used can be a regression by partial least squares (or PLS), whose principle will be recalled hereinafter. More precisely, in one preferred embodiment of the invention, two regressions PLS are carried out: a first for estimating $\rho$ using an extinction curve $\mu'(E_1)$ and a second for estimating $Z_{effm}$ using $D\mu'(E_1)$.

The PLS (Partial Least Squares) method belongs to the prediction methods known as factorial analysis or multivariate analysis methods. Factorial analysis applies a reduction in the number of the easily measurable variables $Y_{var}$ (here, $\mu'$ and $D\mu'$) into a reduced number of linear combinations of the $Y_{var}$, called factors, with the aim of concentrating the useful information into a space of lower dimension and thus allowing a regularization of the inversion by reducing the number of unknowns. The PLS method differs from the methods of the principal component regression (or PCR) or principal component analysis (or PCA) type in that it takes into account both the information on the parameters to be estimated $X_{var}$ (here, $\rho$ and $Z_{effm}$) and on the $Y_{var}$ and $D\mu'$). The PLS method therefore performs an extraction of the eigenvectors from the matrices of parameters X and from the matrices of measurements Y of the calibration mixtures, whereas the methods such as PCR carry out this extraction only from the matrix of the measurements Y.

Several types of PLS regression exist. The simplest, referred to as PLS1, is applicable to the case where the matrix of parameters is a simple vector that is indicated by x (as in the present case, since $\rho$ and $Z_{effm}$ are estimated separately). In the case where several parameters are sought at the same time, X corresponds to a matrix and the PLS2 algorithm is then used. The PLS1 method is described hereinafter:

For each of the K factors to be included in the model (K is to be chosen by the user; in the present case, a single factor will generally be used), the steps of the calibration algorithm are as follows:

Initialization: $Y_0 = Y$ and $x_0 = x$ with:
  Y: the matrix of the calibration measurements of size M by Ne, with M the number of "etalon" materials and Ne the number of energy channels in the curve of measurements (this measurement curve corresponds either to $\mu'(E)$ in the case of the estimation of $\rho$, or $D\mu'(E)$ in the case of the estimation of $Z_{effm}$);
  x: the vector of the useful variables (either $\rho$, or $Z_{effm}$) of size M (the number of etalon materials).

One component of the base-change matrix, referred to as matrix of weights or 'loading vector', $w_k$ is calculated in order to determine the component of $Y_k$ the most correlated with the variations in $x_k$. The objective is to find a vector $w_k$ that generates a vector $t_k$ of maximum covariance with $x_k$:

$$\max_{w_k}[\text{cov}(t_k, x_{k-1}) \mid t_k = Y_{k-1}w_k \text{ and } \|w_k\|^2 = 1] =$$

$$\max_{w_k}\left[x^T t = \sum_{i=1}^{M} x_i t_i \;\middle|\; t_i = \sum_{j=1}^{Ne} y_{ij} w_j \text{ and } \|w\|^2 = 1\right]$$

For a greater readability of the equations, the indices k and k−1 are omitted:

$$= \max_{w_k}\left[\sum_{i=1}^{M}\sum_{j=1}^{Ne} x_i y_{ij} w_j \;\middle|\; \|w\|^2 = 1\right] = \max_{w_k}[Y^T xw \mid \|w\|^2 = 1]$$

Under the constraint that w is unitary, the maximum value of the preceding expression is obtained when w is a colinear unitary vector at $Y^T x$ ("$T$" indicates the transposition operator), being:

$$w_k = \frac{Y_{k-1}^T x_{k-1}}{\|Y_{k-1}^T x_{k-1}\|}$$

The 'score' is subsequently estimated by projecting $Y_{k-1}$ onto $w_k$:

$t_k = Y_{k-1} w_k$

The weighting vector for the measurements $v_k$ is determined by regression of $Y_{k-1}$ over $t_k$ and that for the variables $q_k$ by regressing $x_{k-1}$ over $t_k$:

$$v_k = Y_{k-1}^T t_k (t_k^T t_k)^{-1} \left(\text{solution of } \min_{v_k} \|Y_{k-1} - t_k v_k^T\|^2\right)$$

$$q_k = x_{k-1}^T t_k (t_k^T t_k)^{-1} \left(\text{solution of } \min_{q_k} \|x_{k-1} - t_k q_k^T\|^2\right)$$

The residues $Y_k$ and $x_k$ are formed by deflation by removing the effects of this factor from the data (the information already modeled is thus subtracted):

$Y_k = Y_{k-1} - t_k v_k^T$ $x_k = x_{k-1} - t_k q_k^T$

The method goes back to the second step until the determination of the desired K factors.

At the end of the calibration step, Y and x can then be written in the form:

$$Y = \sum_{k=1}^{K} t_k v_k^T + R$$

$$x = \sum_{k=1}^{K} t_k q_k^T + f$$

with R the matrix of the residues associated with the prediction of Y and f the vector of the residues associated with the prediction of x.

Once the model has been estimated, it is used for the prediction step. During this step, the model and the new data Y are used in order to predict the values of the variables $\rho$ or $Z_{effm}$ based on prediction data. Thus, the information corresponding to each factor with which x ($\rho$ or $Z_{effm}$) is constructed is successively extracted from Y. The procedure is therefore the following:

The vector x is initially zero, k=0;
Calculation of the 'score': $t_k = Y_k w_k$;
Calculation of the contribution of this 'score' on x:

$x_{k+1} = x_k + t_k q_k^T$;

Calculation of the residue:

$Y_{k+1} = Y_k - t_k v_k^T$

Increment of k and iteration up to k=K.

The simultaneous use of the information on x and Y in the calibration step allows better prediction results to be obtained than with the PCR method which only uses the information on Y. In contrast to the principal components analysis, the PLS algorithm searches over the space of the factors conforming closest to the variables x and Y, and so its prediction is better.

Thus, it is possible to extract two parameters characteristic of a material—$\rho$ and $Z_{effm}$—using a combined extinction curve $\mu'(E)$ obtained from X-ray scattering spectra. The material can therefore be represented by a point in the plane $\rho/Z_{effm}$.

Since this material is unknown, the objective is then to identify it using the values of $\rho$ and of $Z_{effm}$, estimated by the method. For this purpose, it is possible to use a set of etalon materials, for which the values of $\rho$ and of $Z_{effm}$ are known, in order to determine a criterion allowing the identification of the unknown material from amongst this database of materials. The criterion used may be a distance criterion in the plane $\rho/Z_{effm}$ with respect to the etalon points, in which case the material will be identified as being the same material as the etalon material with which the estimated distance is the smallest. Otherwise, the criterion used can be a probabilistic criterion (the etalons then make reference to probability distributions) and, in this case, the material will be identified as being that with the highest probability.

Figure 5:
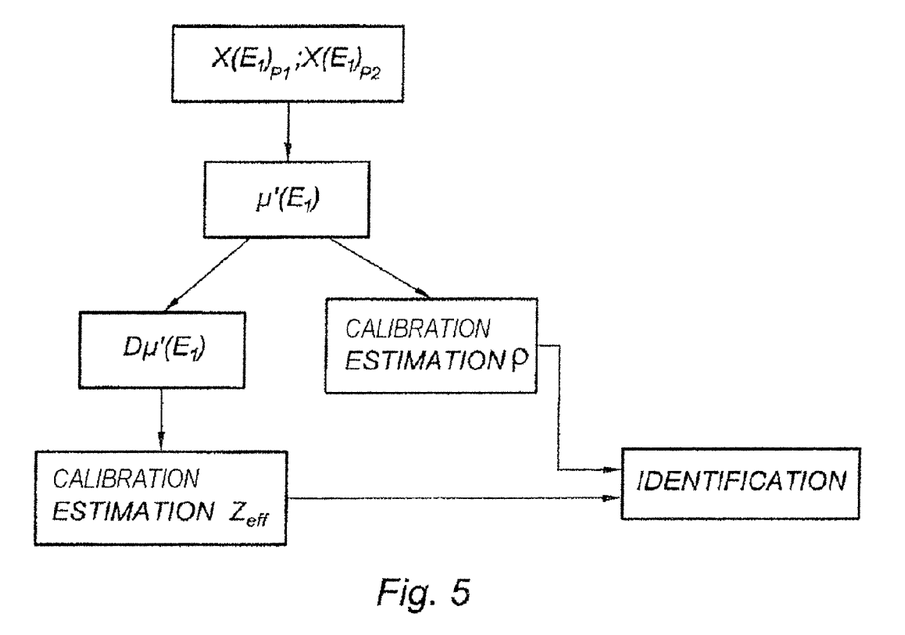
FIG. 5 is a diagram describing a method of identification of a material according to one embodiment of the invention; and The graphs in FIGS. 6A-6E illustrate one exemplary application of the method and of the device of the invention to the identification of a material.

FIG. 5 illustrates diagrammatically the various steps of the method of identification according to the invention. Firstly, spectra $X(E_1)$ are acquired at two depths or more; these spectra are used for estimating the combined extinction curves $\mu'(E_1)$; the extinction curves obtained from known materials are used for calibrating a first multivariate model, then those obtained from unknown materials are used for predicting the densities $\rho$ of said materials with the aid of said first model. In a later step or in parallel, the combined extinction curves $\mu'(E_1)$ are also used for estimating the functions $D\mu'(E_1)$. The functions $D\mu'(E_1)$ obtained from known materials are used for calibrating a second multivariate model, then those obtained from unknown materials are used for predicting the mass effective atomic numbers $Z_{effm}$ of said materials with the aid of said second model. Lastly, the unknown materials are represented by points in the plane $\rho/Z_{effm}$, and their identification is carried out. These operations are carried out en using an information processing means.

It will be understood that it is not always necessary to implement all the steps of the method; for example, it may be sufficient to estimate the density and/or the mass effective atomic number of a material without necessarily wanting to identify it. Also, other parameters rather than $\rho$ and $Z_{effm}$ can be estimated, by potentially using other functions coming from the scattering spectra than $\mu'$ and $D\mu'$.

The method of the invention has been validated experimentally. The device in FIG. 1 has been used for analyzing a cubic block of 0.5 dm³ of polyvinylidiene fluoride, whose characteristics are as follows: $\rho=1.79$ g/cm³; $Z_{effm}=7.62$. This known material was assumed to be unknown for the purposes of the validation of the method.

Figure 6A:
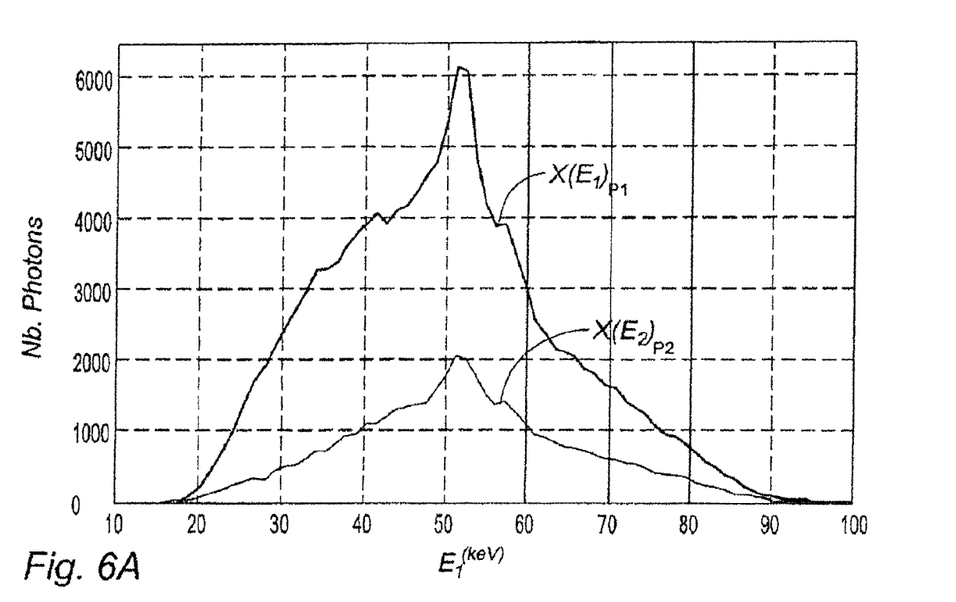
Figure 6B:
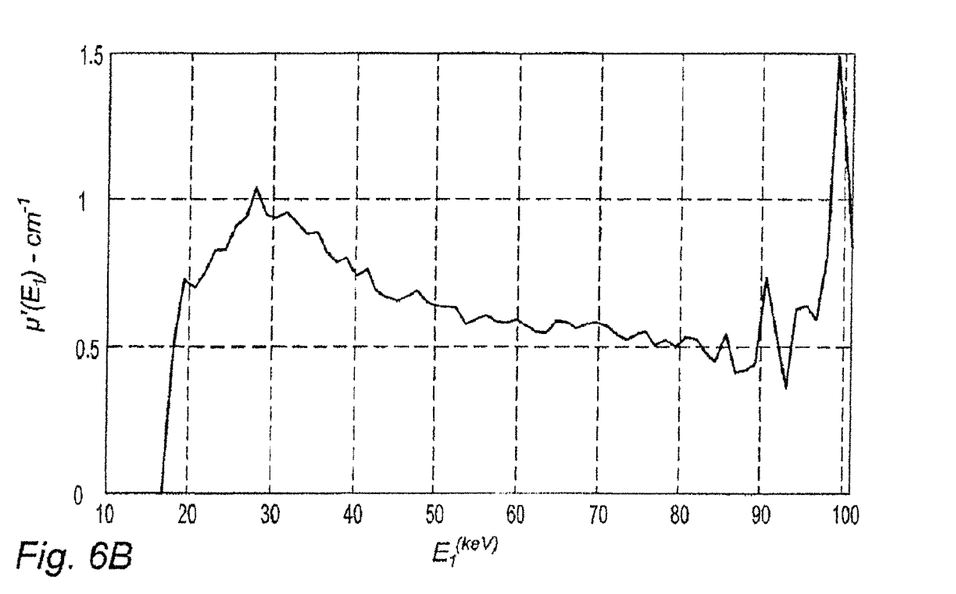
Figure 6C:
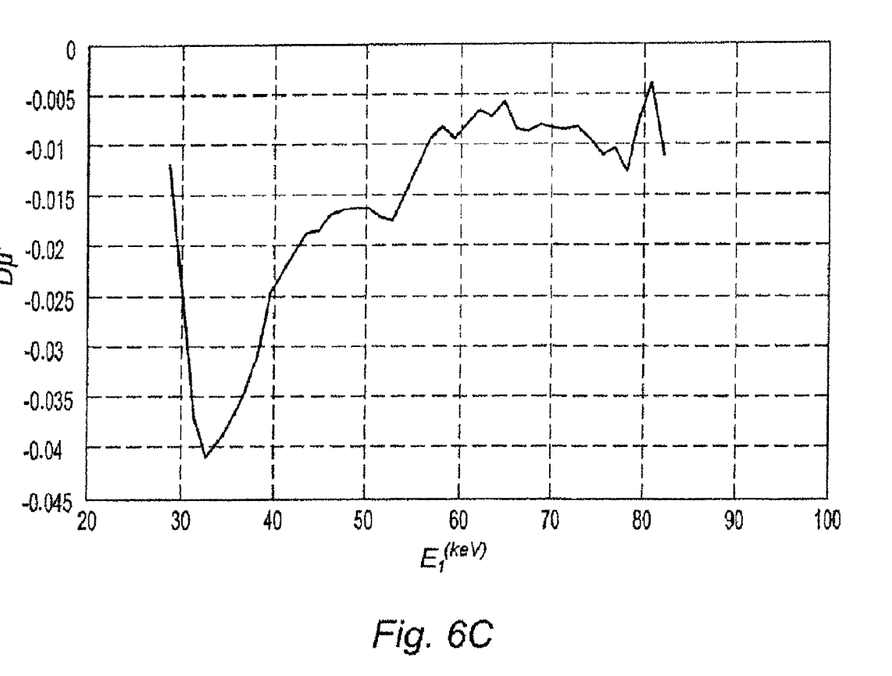

Measurements of spectra in backscattered radiation ($\theta=120°$) have therefore been carried out at two depths in the material: $P_1=15$ mm, $P_2=30$ mm. The spectra obtained, $X(E_1)_{P1}$ and $X(E_1)_{P2}$, are reproduced in FIG. 6A. FIG. 6B shows the combined extinction curve obtained by applying the equation (3) to these spectra, in the range 18-100 keV. FIG. 6C shows the corresponding curve of the function $D\mu'$, defined according to the equation 6'.

In a first example, the calibration database used for constructing the two models includes the material to be identified. The calibration database thus includes polyvinylidiene fluoride, polyformaldehyde, polytetrafluoroethylene, water, polymethylmethacrylate and nylon. The model has been constructed from the six combined extinction curves corresponding to these materials. The curve of the "unknown" material (in fact, polyvinylidiene fluoride) was subsequently used for the prediction step. The values predicted for the density and the mass effective atomic number are:

$$\hat{\rho}=1.756 \text{ g/cm}^3$$

$$\hat{Z}_{effm}=7.439.$$

Figure 6D:
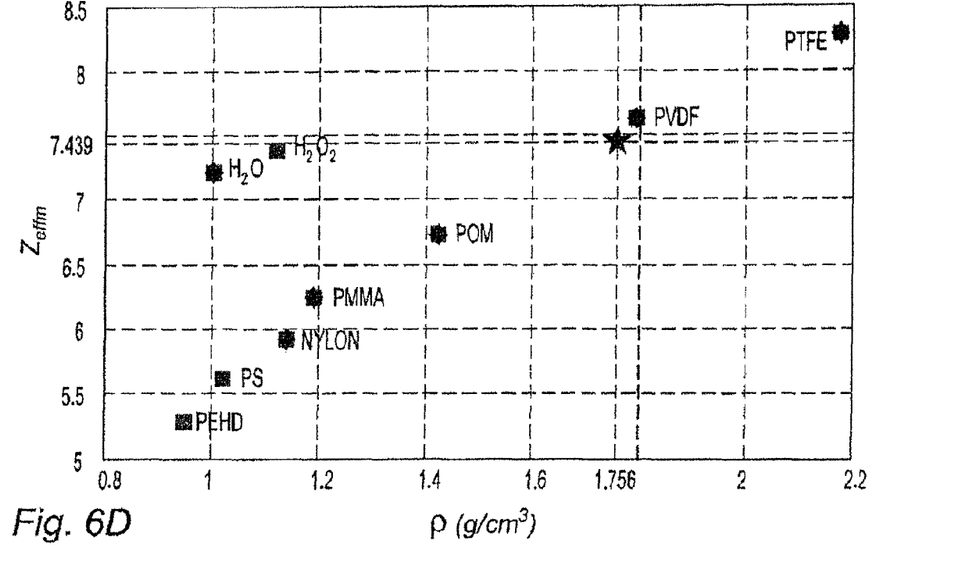

These values constitute the coordinates of a point (represented by a star in FIG. 6D) in the plane $\rho/Z_{effm}$; other reference materials are also represented by points in this plane (the squares correspond to the materials from the identification database; the diamonds, to the materials from the database for construction of the model). The "unknown" material is recognized as being polyvinylidiene fluoride by application of a simple minimum distance criterion.

In a second example, it has been chosen to exclude polyvinylidiene fluoride from the calibration database (indeed, under real conditions, it is not very likely that the unknown material will be included in this database); the models have therefore been constructed using five calibration curves corresponding to polyformaldehyde, to polytetrafluoroethylene, to water, to polymethylmethacrylate and to nylon.

The values predicted for the density and the mass effective atomic number are:

$$\hat{\rho}=1.763 \text{ g/cm}^3$$

$$\hat{Z}_{effm}=7.423.$$

Figure 6E:
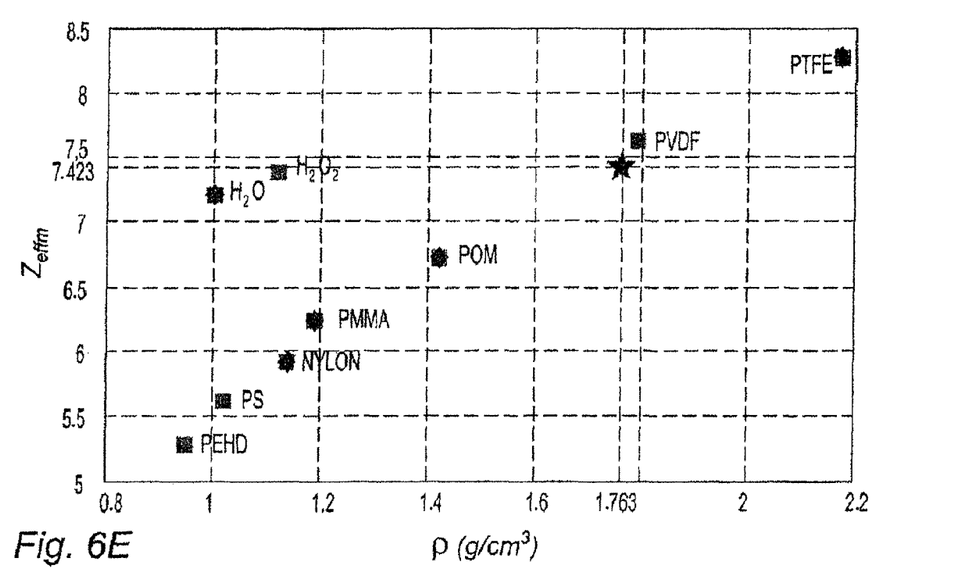

The estimation is not therefore significantly degraded with respect to the previous case, where the material to be characterized appears in the calibration database. As FIG. 6E shows, the identification of the material is also possible in this case.

The invention claimed is:

1. A method for characterizing a material comprising the steps:
   a. directing a first collimated beam of electromagnetic radiation, of energy greater than or equal to 1keV, towards a sample of the material to be characterized;
   b. acquiring a spectrum of a second beam of electromagnetic radiation, obtained by scattering of said first beam by an elementary volume of said sample through a predefined scattering angle $\theta$;
   said steps a and b being repeated one or more times, each time modifying the lengths of the paths of the first and of the second beam inside of said material, while at the same time maintaining substantially constant their ratio $\epsilon$ together with said scattering angle $\theta$; and
   c. estimating one or more properties characteristic of said material based on the spectra acquired during the repetitions in the step b;
   said step c being implemented by means of at least one multivariate model, and comprising a calculation, based on the spectra acquired during the repetitions of said b, of a combined linear extinction function $\mu'$ of the material, defined as a weighted average of the linear extinction coefficients $\mu$ of the material for the electromagnetic radiation incident at an energy E0 and for the electromagnetic radiation scattered at an energy $E_1$ where E0 represents the energy of an incident photon and $E_1$ that of a photon having undergone a scattering through said scattering angle $\theta$, a weighting coefficients of said average depending on said ratio $\epsilon$, said combined linear extinction function being expressed as a function of an energy chosen from between E0 and $E_1$;
   wherein said step (c) also comprises: —a determination of a function $D\mu'$ representative of a comparison between values taken by said combined linear extinction function $\mu'$ for values of energy having a constant difference dE; and —an estimation of a mass effective atomic number of said material based on the values of said function $D\mu'$ for a plurality of values of energy, by application of said at least one multivariate model.

2. The method as claimed in claim 1, in which said step (c) also comprises an estimation of a density of said material based on the values of said combined linear extinction function for a plurality of values of energy, by application of said at least one multivariate model.

3. The method as claimed in claim 1, in which said step (c) also comprises an estimation of a density of said material based on the values of said combined linear extinction function for a plurality of values of energy, by application of a first multivariate model, and also comprising a step for identification of said material based on the estimated values of its density and on its mass effective atomic number.

4. The method as claimed in claim 1, in which said multivariate model is based on a regression by partial least squares.

5. The method as claimed in claim 1, in which said steps a and b are repeated one or more times, each time modifying a depth of said elementary volume of the sample with respect to a surface of incidence of said collimated beam of electromagnetic radiation.

6. The method as claimed in claim 5, in which said depth of said elementary volume of the sample is modified by rigid translation of a source and of a spectrometric sensor of electromagnetic radiation with respect to said sample, in a direction perpendicular to said surface of incidence.

7. The method as claimed in claim 1, in which said material is an organic material.

8. The method as claimed in claim 1, in which said first collimated beam of electromagnetic radiation is polychromatic and exhibits an energy spectrum extending over at least 10 keV in a region within the range between 10 keV and 300 keV.

9. A device for characterizing a material comprising:
a collimated source of electromagnetic radiation of energy greater than or equal to 1 keV, configured for directing a first collimated beam of electromagnetic radiation towards a sample of the material to be characterized;
a spectrometric sensor for electromagnetic radiation, configured for acquiring a spectrum of a second beam of electromagnetic radiation, obtained by scattering of said first beam by an elementary volume of said sample through a predefined scattering angle;
an actuation system, configured for modifying a relative position of said source and of said spectrometric sensor with respect to said sample in such a manner as to modify the lengths of the paths of the first and of the second beam inside of said material, while at the same time maintaining substantially constant their ratio c together with said scattering angle $\theta$; and
a means for processing information, configured or programmed for estimating one or more properties characteristic of said material based on a plurality of spectra acquired by said spectrometric sensor for various values of said lengths of the paths of the first and of the second beam inside of said material;
wherein said means for processing the information is configured or programmed for estimating one or more properties characteristic of said material by means of at least one multivariate model, and wherein said means for processing the information is configured or programmed for calculating, based on the spectra acquired, a combined linear extinction function $\mu'$ of the material, defined as a weighted average of linear extinction coefficients $\mu$ of the material for the electromagnetic radiation incident at an energy $E_0$ and for the electromagnetic radiation scattered at an energy $E_1$, where $E_0$ represents the energy of an incident photon and $E_1$ that of a photon having undergone a scattering through said scattering angle $\theta$, a weighting coefficients of said average depending on said ratio $\epsilon$, said combined linear extinction function being expressed as a function of an energy chosen from between $E_0$ and $E_1$, and in which said means for processing the information is configured or programmed for determining a function $D\mu'$ representative of a comparison between values taken by said combined linear extinction function $\mu'$ for values of energy having a constant difference dE; and estimating a mass effective atomic number of said material based on values of said function $D\mu'$ for a plurality of values of energy, by application of said at least one multivariate model.

10. The device as claimed in claim 9, in which said means for processing the information is configured or programmed for estimating a density of said material based on values of said combined linear extinction function for a plurality of values of energy, by application of said multivariate model.

11. The device according to claim 9, in which said means for processing the information is configured or programmed for determining a function $D\mu'$ representative of a comparison between values taken by said combined linear extinction function for values of energy having a constant difference dE; and estimating a mass effective atomic number of said material based on values of said function $D\mu'$ for a plurality of values of energy, by application of a second multivariate model.

12. The device as claimed in claim 9, in which said means for processing the information is configured or programmed for estimating a density of said material based on values of said combined linear extinction function for a plurality of values of energy, by application of said multivariate model, and wherein in which said means for processing the information is configured or programmed for identifying said material based on the estimated values of its density and of its mass effective atomic number.

13. The device according to claim 9, in which said multivariate model is based on a regression by partial least squares.

14. The device as claimed in claim 9, in which said actuation system is designed to modify a depth of said elementary volume of the sample with respect to a surface of incidence of said collimated beam of electromagnetic radiation by rigidly translating said source and said spectrometric sensor with respect to said sample, in a direction perpendicular to said surface of incidence.

15. The device as claimed in claim 9, in which said collimated source of electromagnetic radiation is polychromatic and exhibits an energy spectrum extending over at least 10 keV in a region within the range between 10 keV and 300 keV.

* * * * *

UNITED STATES PATENT AND TRADEMARK OFFICE
CERTIFICATE OF CORRECTION

PATENT NO. : 9,535,017 B2  
APPLICATION NO. : 14/352774  
DATED : January 3, 2017  
INVENTOR(S) : Paulus et al.

Page 1 of 1

It is certified that error appears in the above-identified patent and that said Letters Patent is hereby corrected as shown below:

In the Claims

Column 13,
Line 43, "ratio c" should read --ratio ε--.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*